United States Patent
Grimm et al.

(10) Patent No.: US 11,959,987 B2
(45) Date of Patent: Apr. 16, 2024

(54) METHOD FOR AN ADAPTIVE ACTUATION OF A MAGNETIC RESONANCE DEVICE

(71) Applicant: Siemens Healthcare GmbH, Erlangen (DE)

(72) Inventors: Robert Grimm, Nuremberg (DE); Berthold Kiefer, Erlangen (DE); Heinrich von Busch, Uttenreuth (DE)

(73) Assignee: Siemens Healthineers AG, Erlangen (DE)

( * ) Notice: Subject to any disclaimer, the term of this patent is extended or adjusted under 35 U.S.C. 154(b) by 0 days.

(21) Appl. No.: 17/025,108

(22) Filed: Sep. 18, 2020

(65) Prior Publication Data
US 2021/0088614 A1 Mar. 25, 2021

(30) Foreign Application Priority Data
Sep. 20, 2019 (DE) .................. 102019214359.8

(51) Int. Cl.
*G01R 33/54* (2006.01)
*A61B 5/055* (2006.01)
*G01R 33/56* (2006.01)
*G06T 7/00* (2017.01)

(52) U.S. Cl.
CPC .......... *G01R 33/543* (2013.01); *A61B 5/055* (2013.01); *G01R 33/5602* (2013.01); *G01R 33/5608* (2013.01); *G06T 7/0012* (2013.01); G06T 2207/20081 (2013.01)

(58) Field of Classification Search
CPC ............. G01R 33/543; G01R 33/5602; G01R 33/5608; A61B 5/055; G06T 7/0012; G06T 2207/20081
See application file for complete search history.

(56) References Cited

U.S. PATENT DOCUMENTS

| | | | |
|---|---|---|---|
| 9,476,955 B2* | 10/2016 | Stemmer | G01R 33/4835 |
| 11,073,584 B2* | 7/2021 | Takeshima | G01R 33/4824 |
| 2004/0037820 A1* | 2/2004 | Alitalo | C07K 14/71 |
| | | | 424/94.4 |
| 2010/0013475 A1 | 1/2010 | Kimura | |
| 2010/0232667 A1* | 9/2010 | Azar | A61B 5/415 |
| | | | 382/131 |

(Continued)

FOREIGN PATENT DOCUMENTS

| | | |
|---|---|---|
| DE | 102006055084 A1 | 6/2008 |
| DE | 102017221830 A1 | 6/2019 |
| WO | 2006034334 A2 | 3/2006 |

OTHER PUBLICATIONS

German action dated Jun. 8, 2020, Application No. 10 2019 214 359.8.

*Primary Examiner* — Dixomara Vargas
(74) *Attorney, Agent, or Firm* — Banner & Witcoff Ltd.

(57) ABSTRACT

In a method for an actuation of a magnetic resonance device for capturing image data from an examination region of an examination object, at least one first control sequence is provisioned, the magnetic resonance device is actuated according to the at least one first control sequence to capture first data from the examination object, the first data is analyzed with respect to a property to generate a result, and, based on the result, a selective performance of one of: a selection of a further control sequence, and termination of the actuation of the magnetic resonance device, is performed.

19 Claims, 2 Drawing Sheets

(56) References Cited

U.S. PATENT DOCUMENTS

| | | | | |
|---|---|---|---|---|
| 2012/0003160 A1* | 1/2012 | Wolf | A61B 5/415 | |
| | | | | 424/9.32 |
| 2012/0052080 A1* | 3/2012 | Okada | A61P 37/04 | |
| | | | | 424/184.1 |
| 2012/0268130 A1* | 10/2012 | Fautz | G01R 33/4616 | |
| | | | | 324/318 |
| 2013/0271133 A1* | 10/2013 | Snyder | G01R 33/4824 | |
| | | | | 324/309 |
| 2015/0038827 A1* | 2/2015 | Yamagata | A61B 6/481 | |
| | | | | 600/411 |
| 2016/0077180 A1* | 3/2016 | Beck | G01R 33/56509 | |
| | | | | 324/309 |
| 2016/0174919 A1* | 6/2016 | Ahn | A61B 5/0059 | |
| | | | | 382/131 |
| 2017/0007148 A1* | 1/2017 | Kaditz | A61B 5/055 | |
| 2017/0131376 A1* | 5/2017 | Miyazaki | G01R 33/56316 | |
| 2017/0153310 A1* | 6/2017 | Bi | G01R 33/543 | |
| 2017/0219672 A1* | 8/2017 | Miyazaki | G01R 33/5614 | |
| 2017/0254869 A1* | 9/2017 | Miyazaki | G01R 33/4822 | |
| 2017/0269182 A1* | 9/2017 | Beck | G01R 33/56509 | |
| 2017/0356973 A1* | 12/2017 | Wheaton | G01R 33/4833 | |
| 2018/0136300 A1* | 5/2018 | De Rochefort | G01R 33/54 | |
| 2019/0016720 A1 | 1/2019 | Patil et al. | | |
| 2019/0156477 A1* | 5/2019 | Perrin | G16H 15/00 | |
| 2019/0167203 A1* | 6/2019 | Paul | G01R 33/543 | |
| 2019/0178965 A1* | 6/2019 | Paul | G01R 33/5659 | |
| 2019/0183561 A1* | 6/2019 | Hobbs | A61B 18/1492 | |
| 2019/0374168 A1* | 12/2019 | Grodzki | G01R 33/563 | |
| 2019/0377047 A1* | 12/2019 | Chen | G01R 33/4818 | |
| 2020/0069214 A1* | 3/2020 | Takeshima | G01R 33/385 | |
| 2020/0158806 A1* | 5/2020 | Okamoto | G01R 33/543 | |
| 2021/0219862 A1* | 7/2021 | Loecher | A61B 5/748 | |

* cited by examiner

FIG 1

METHOD FOR AN ADAPTIVE ACTUATION OF A MAGNETIC RESONANCE DEVICE

CROSS REFERENCE TO RELATED APPLICATIONS

This patent application claims priority to German Patent Application No. 102019214359.8, filed Sep. 20, 2019, which is incorporated herein by reference in its entirety.

BACKGROUND

Field

The disclosure relates to a method, a magnetic resonance device, a computer program product and an electronically readable data carrier for an actuation of a magnetic resonance device for capturing image data from an examination region of an examination object.

Related Art

In a magnetic resonance device, the body of an examination object to be examined, particularly that of a patient, is typically exposed to a relatively strong main magnetic field of, for example, 1.5 or 3 or 7 tesla, with the aid of a main magnet. In addition, gradient pulses are played out with the aid of a gradient coil unit. High-frequency radio-frequency pulses, for instance excitation pulses, are then transmitted via a radio-frequency antenna unit by means of suitable antenna facilities, with the result that the nuclear spins of particular atoms resonantly excited by these radio-frequency pulses are tilted by a defined flip angle compared to the magnetic field lines of the main magnetic field. When the nuclear spins are relaxed, radio-frequency signals known as magnetic resonance signals are emitted, and are received and then further processed using suitable radio-frequency antennas. From the raw data acquired in this way, the desired image data can ultimately be reconstructed.

For a particular scan, a particular control sequence, also known as a pulse sequence, which consists of a sequence of radio-frequency pulses, for example excitation pulses and refocusing pulses, as well as gradient pulses to be transmitted suitably coordinated therewith on various gradient axes along different spatial directions, is therefore to be transmitted. Timed to coincide with this, readout windows are set which define the time periods in which the induced magnetic resonance signals are detected. The generation and controlled interaction of the main magnetic field with the gradient pulses, the radio-frequency pulses, i.e. the output of a control sequence or of several control sequences, can be referred to as an actuation of the magnetic resonance device.

The examination region is a spatial subregion of the examination object from which image data is generated upon actuation of the magnetic resonance device. For an examination and/or arrival at a diagnosis of an examination object, in particular of a patient, by means of a magnetic resonance device, image data from the examination region is typically generated in different contrasts and/or spatial orientations. A control sequence typically specifies a rule for actuation of the magnetic resonance device for generating image data with a contrast. A contrast determines a visibility of a first tissue compared to a second tissue. A particular contrast can characterize a particular tissue property. An actuation of the magnetic resonance device according to different control sequences is therefore required for arriving at a diagnosis of an examination object. These various control sequences typically differ as regards the temporal sequence and/or the number of gradient pulses, radio-frequency pulses, and/or the points in time at which the magnetic resonance signals are received. The various control sequences can differentiate themselves by administering a contrast agent to the examination object. The various control sequences can differentiate themselves by means of further parameters.

The contrasts of image data required in the context of an examination and correspondingly the control sequences to be used typically depend on the suspicion regarding an illness and/or a diagnosis to be expected and/or the purpose of the examination of the examination object. There are examinations which require an actuation of the magnetic resonance device with ten or more control sequences.

The control sequences to be used are conventionally specified as a set depending on the type of examination and/or the organ to be examined. A set is typically adapted in such a way that a diagnosis is possible. The set, in particular the type, the sequence and the precise parameters of the control sequences, are selected or adapted once by the radiologist and/or user of a particular magnetic resonance device. In addition to the type of examination and/or the organ to be examined, the set can be dependent on a particular imaging strategy. Imaging strategies can for example characterize a breathholding capacity and/or a staying-still capacity of the examination object and/or a maximum duration of the overall examination. In this way a movement-robust imaging strategy can be selected for patients who are uncooperative and/or are unable to hold their breath.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

An object of the disclosure is to specify a particularly flexible and adaptive method for actuating a magnetic resonance device.

In an exemplary embodiment, the method for an actuation of a magnetic resonance device for capturing image data from an examination region of an examination object includes the following method steps:

Provision of at least one first control sequence,

Actuation of the magnetic resonance device according to the at least one first control sequence, wherein first data is captured from the examination object, Analysis of the first data as regards a property, wherein a result is generated, Selection of one of the two following options based on the result: Selection of a further control sequence or termination of the actuation of the magnetic resonance device.

In an exemplary embodiment, the method is executed in an actuation unit. The provision of the at least one first control sequence typically takes place via an input included in the actuation unit. In an exemplary embodiment, a control sequence is a sequence of self-contained radio-frequency pulses and gradient pulses, by means of which raw data of the examination region is acquired, it being possible for said raw data to be reconstructed into image data, wherein the image data maps the examination region. An actuation of the magnetic resonance device according to a control sequence comprises the playing out of the sequence of radio-frequency pulses and gradient pulses provided by the control sequence by means of the magnetic resonance device.

The first data can be raw data. Raw data is, for example, data which is present in the k-space. The first data can be image data. The first data can be preprocessed and/or postprocessed image data. In an exemplary embodiment, the first data includes a spatially resolved signal intensity in the k-space and/or in the image space.

In an exemplary embodiment, the analysis of the first data as regards a property comprises a check as to whether the first data has the property, and/or an extraction of the property from the first data. The analysis can, for example, comprise a registration of the first data to reference data and/or a segmentation of a subregion of the examination region. The analysis can comprise a statistical evaluation, in particular a determination of an average value, a deviation, and/or the creation of a histogram based on the first data. The result is typically a binary or quantitative value. The result can for example stipulate whether and to what extent the first data has the property. The analysis of the first data as regards a property typically takes place at a point in time, at which point in time the examination object is arranged in a largely unchanged position, the examination object having said position during the actuation of the magnetic resonance device according to the at least one first control sequence.

In an exemplary embodiment, based on the result, the method according to the disclosure provides for a choice of two options. Upon selection of a further control sequence, an actuation of the magnetic resonance device according to the further control sequence preferably takes place in a following method step.

Upon selection of a further control sequence, two or more further control sequences can also be selected, according to which the magnetic resonance is actuated as part of the examination according to the two or more further control sequences. In an exemplary embodiment, the selection of a further control sequence comprises an actuation of the magnetic resonance device according to the further control sequence, wherein further data from the examination object, preferably within the examination region, is captured.

The further control sequence can correspond to a control sequence of the at least one first control sequence. This can for example be the case provided the quality of the first data lies below a threshold value. The further control sequence can differ from the at least one first control sequence. The selection of the further control sequence can comprise a choice of a further control sequence from a list comprising a multitude of control sequences. The selection and/or choice typically takes place based on the result and/or the property and/or the at least one first control sequence according to which the magnetic resonance device was previously actuated. The further control sequence can be selected in such a way that the further data to be generated upon actuation of the magnetic resonance device by means of the further control sequence generates a contrast which is relevant for a diagnosis of an illness, it being possible for said illness to be indicated and/or excluded on the basis of the result.

Upon termination of the actuation of the magnetic resonance device, the recording of data from the examination object, in particular from the examination region of the examination object, stops. Upon termination of the actuation of the magnetic resonance device, the examination of the examination object by means of the magnetic resonance device is typically interrupted and/or stopped for at least one hour, preferably for at least one day, particularly preferably for at least one week. An actuation of the magnetic resonance device to record image data from a further examination object typically follows the termination of the actuation of the magnetic resonance device. Upon termination of the actuation of the magnetic resonance device, an arrival at a diagnosis can take place based on the first data.

The method according to the disclosure is typically carried out in the context of an examination of the examination object. An examination is characterized in that the examination object does not leave the room in which the magnetic resonance device is arranged for the duration of the examination. An examination can be characterized in that the examination object does not change its position for the duration of the examination.

In an exemplary embodiment, the method allows an adaptive adjustment of the actuation of the magnetic resonance device. Based on the result and/or the first data, the actuation of the magnetic resonance device can be ended or continued according to a further control sequence. It can therefore be decided, depending on a property and/or the result, whether for example further data is required. It can be decided, depending on a property and/or the result, which further data is required. A flexible choice of a further control sequence allows an efficient actuation of the magnetic resonance device. In particular, further data can be recorded individually for a potential illness based on results of the first data, wherein the type and/or quantity of further data can be selected based on previous results. The possible choice of a further control sequence allows a needs-driven, extensive diagnosis of the examination object and/or gradual and justified procedure for the actuation of the magnetic resonance device depending on the examination region. The further data can also be recorded individually based on the capability of the examination object for cooperation with the capture of the first data. The further control sequence can therefore for example correspond to the first control sequence, provided the examination object negatively influenced the first data due to movement. In this case however a more patient-friendly, for example shorter, further control sequence can also be selected compared to the first control sequence.

A defined set of control sequences are conventionally stipulated for an examination. In an exemplary embodiment, the method according to the disclosure enables an individual adjustment of the set, also during the examination. In an exemplary embodiment, the method according to the disclosure enables an individual choice of the control sequences for actuation of the magnetic resonance device depending on the results from the first data already recorded. The choice of an option allows an individual and adaptive compilation of relevant control sequences for the examination object, which are used as part of the examination. In this way unnecessary control sequences can be dispensed with and if required at least one dedicated relevant further control sequence can be selected. As a result a diagnosis can be improved and/or the duration of the examination can be reduced. This enables cost saving and improved patient comfort.

An embodiment of the method provides that the method comprises a provision of a trained function and/or of a neural network and the analysis of the first data takes place by means of the trained function.

In an exemplary embodiment, the neural network and/or the trained function are trained in advance as regards at least one property. In an exemplary embodiment, the neural network and/or the trained function are trained in advance for the examination region, wherein at least one property, preferably several properties, relevant for this examination region were taken into consideration. For example, the neural network and/or the trained function can be embodied to support the analysis of the first data as regards a movement and/or a susceptibility artifact and/or a presence of a lesion as a property.

In an exemplary embodiment, the neural network and/or the trained function are trained in advance by means of a plurality of medical image data as regards the property and/or the result. The plurality of medical image data can include at least partially a structure included in the examination region. The plurality of medical image data preferably originates from a plurality of examination objects. In an exemplary embodiment, the neural network and/or the trained function are trained in advance for a computer-aided diagnosis and/or computer-aided detection, preferably for a structure included at least partially in the examination region.

The neural network and/or the trained function can be embodied for an extraction of the property from the first data. This can, for example, comprise a segmentation of a structure. The neural network and/or the trained function is preferably embodied in the event of a termination of the actuation of the magnetic resonance device to arrive at a diagnosis based on the first data, typically taking into consideration the property and the result. The neural network and/or the trained function is preferably embodied to execute the choice between a selection of a further control sequence and the termination of the actuation of the magnetic resonance device. The neural network and/or the trained function is preferably embodied in the event of a choice of a selection of a further control sequence to execute the embodiment of the further control sequence.

The neural network and/or the trained function is embodied according to this embodiment to generate the result. The neural network and/or the trained function is preferably embodied to provide the result via an output. The neural network and/or the trained function is typically applied by an actuation unit or by a processor unit comprised within an actuation unit.

This embodiment allows a particularly precise analysis of the first data as the neural network and/or the trained function are based on a plurality of such results and/or data. This embodiment allows a particularly objective analysis of the first data as regards the property. This embodiment also allows an analysis of the first data as regards several properties simultaneously. Such an analysis typically exceeds the visual detection of a radiologist. On the one hand this allows a better diagnosis based on the first data. On the other hand if required a further control sequence can be soundly selected.

In an exemplary embodiment, the method provides that the selection comprises an automatic preselection of one of the two options and a confirmation of the preselection by a user.

If the preselection comprises the selection of a further control sequence as the selected option, the preselection preferably also comprises the selection of the further control sequence, said further control sequence being made available to a user for confirmation. The user is typically a medically technically trained specialist or a radiologist.

This embodiment allows an improved operation of the magnetic resonance device by the user. In particular this embodiment allows the user to influence the actuation of the magnetic resonance device. The user can regularly confirm and accept the preselection. Acceptance by the user is typically followed by the actuation of the magnetic resonance device according to the further control sequence or by the end of the examination. With this embodiment the user has the option to react depending on the situation. For example wishes of the examination object can be taken into consideration and/or external influences such as an emergency examination with the magnetic resonance device of another examination object can influence the confirmation by the user. As a result the user is particularly flexible.

In an exemplary embodiment, the method provides that the property comprises at least one of the following features:
an artifact,
a susceptibility artifact,
a lesion, in particular a focal lesion,
a cyst,
a hemangioma,
a size of a structure,
a texture of a structure,
a movement of the examination object during the actuation of the magnetic resonance device according to the at least one first control sequence,
a quality of the first data, and/or
an abnormality.

A cyst and a hemangioma are examples of a lesion of the liver. A movement of the examination object during the actuation of the magnetic resonance device and a susceptibility are examples of causes for artifacts.

A lesion is typically an example of an abnormality of a morphology. An abnormality can relate to a morphology and/or a function of the examination region and/or a quality of the first data.

The analysis of the first data typically takes place as regards at least one of the above-mentioned features. Depending on the type of the first data these can be analyzed as regards one of the above-mentioned features. If the first data comprises image data and/or the analysis comprises a reconstruction of the first data into image data, the analysis can comprise a segmentation, registration and/or an image processing. In this way a structure, such as for example an organ, a lesion, a cyst and/or a hemangioma can be identified and/or segmented. Within this structure, as part of the analysis based on a signal intensity of the image data within the structure, a texture of the structure can be determined. Likewise a size of the structure, for example a volume and/or a form of the structure can be determined.

Such a property can be an indication of an abnormality and/or a particular illness. Based on such a finding a further control sequence can be selected in the context of the actuation for a confirmation of the abnormality and/or illness.

Likewise the first data can indicate an artifact, in particular a susceptibility artifact and/or a movement of the examination object. Here, if required, the at least one control sequence can be selected as a further control sequence and repeated. A susceptibility artifact is typically a local dropping out of a signal in image data based on a local change in the static magnetic field, for example induced by changes in susceptibility in the tissue. The analysis typically comprises an analysis of the first data as regards two or more properties.

This embodiment allows a set of control sequences to be dynamically adapted depending on different features. The specified features allow a diverse application area and an identification of different diseases. This embodiment of the method can therefore be applied particularly flexibly, also for different investigations. Likewise the duration of the examination can be reduced for many diagnoses and/or administering contrast agent can be avoided. As contrast agents have side effects for the examination objects, the risk of the examination can be reduced. Likewise the quality of the data captured during the examination can be improved by capturing additional data with the further control sequence.

An embodiment of the method provides that the result comprises a presence of the property and/or a comparison of a value which characterizes the property with a reference value. The value characterizing the property and/or the reference value is typically a quantitative value.

The reference value is typically a fixed predetermined value for a property. The reference value can for example be a threshold value for a property. The reference value can be based on the property of a plurality of examination objects. The reference value can be an empirically determined value for the property, on the basis of which a presence of a disease can be characterized. If the result comprises a comparison of a value characterizing the property with a reference value, exceeding or not reaching the threshold value can indicate an illness and/or diagnosis. The result can be a biomarker or surrogate marker.

Based on such a result, the further approach can be particularly well determined, thus a decision between the two options can be decided on particularly effectively. In particular the selection of a further control sequence can be aligned particularly precisely to an illness and/or diagnosis indicated by the result. In this way the examination can be tailored to the individual and the examination time can be used efficiently.

An embodiment of the method provides that the result comprises a presence of a susceptibility artifact and, when choosing, a selection of a further control sequence for reducing metal artifacts takes place.

A susceptibility artifact can for example be induced by a metal implant, such as for example an artificial hip joint. Control sequences exist which can efficiently compensate such a susceptibility artifact. Examples of such control sequences are VAT, spin-echo sequence with high bandwidth of the RF pulses, SEMAC and MAVRIC. Due to their duration, these control sequences are not typically used in a conventional set of control sequences. This embodiment allows an automatic and dynamic adjustment of impairments in the quality of the first data and the selection of a suitable further control sequence to improve the quality.

An embodiment of the method provides that the result comprises a presence of a movement above a threshold value and, when choosing, a selection of a movement-insensitive control sequence takes place.

A movement-insensitive control sequence is typically a control sequence which is robust as regards a movement of the examination object, in particular generates data which is largely independent of a movement of the examination object. The result can also already be generated during the capture of the first data. This embodiment allows an adjustment of the examination for examination objects for which a calm positioning or a positioning with minimal movement is problematic.

An embodiment of the method provides that the examination region is a prostate, upon actuation of the magnetic resonance device according to the at least one first control sequence an actuation of the magnetic resonance device takes place according to a T2-weighted control sequence and a diffusion-weighted control sequence, and the first data comprises T2-weighted data and diffusion-weighted data.

The T2-weighted data and the diffusion-weighted data are typically image data. In the case of a prostate, T2-weighted data and/or diffusion-weighted data, which are generated by means of the at least one first control sequence, can typically indicate a presence of a tumor. In particular, the analysis of the first data comprising T2-weighted data and diffusion-weighted data of the examination region, i.e. the prostate, a combined evaluation of the T2-weighted data and diffusion-weighted data as regards a property, in particular as regards a presence of a tumor, can take place. The first data according to this embodiment is typically sufficient to rule out a presence of a tumor.

If the result comprises for example that a lesion and/or a tumor can be ruled out, at the selection stage a termination of the actuation of the magnetic resonance device preferably takes place.

Likewise the result, in particular based on the T2-weighted data can comprise that a lesion with a diameter of more than 10 mm, in particular of more than 15 mm is present within the examination region. In this situation a termination of the magnetic resonance device can take place at the selection stage. Further data acquired by means of a further control sequence, in particular a perfusion-weighted control sequence, would not deliver any further relevant information as regards the lesion.

If a termination of the actuation of the magnetic resonance device follows this embodiment, the need to administer a contrast agent, which can be required for a perfusion-weighted control sequence, can then in particular be eliminated. Likewise the duration of the examination can be shortened.

This embodiment thus enables an informative basis as regards a disease of the prostate, in particular at an early stage after an actuation of the magnetic resonance device according to a T2-weighted control sequence and a diffusion-weighted control sequence. This informative basis can in particular enable an efficient further process of the examination by means of a dedicated selection of an option. This embodiment of the method is particularly suited to a preventive health check, during which the need to administer contrast agent can initially be eliminated. A further control sequence is typically initiated only in the case of a positive finding.

An embodiment of the method provides that the result comprises a presence of a lesion and, when choosing, a selection of a perfusion-weighted control sequence as the further control sequence takes place.

The perfusion-weighted control sequence is typically a dynamic contrast agent perfusion sequence and is based on the measurement of the contrast agent passage through the tissue which is of interest. Following selection of the perfusion-weighted control sequence, an actuation of the magnetic resonance device preferably takes place according to the profusion-weighted control sequence, wherein further data comprising perfusion-weighted data is generated.

In the case of the presence of a lesion, in particular a lesion within the transition zone or the peripheral zone of the prostate, and/or in the case of the presence of a lesion with a diameter less than 15 mm, in particular less than 10 mm, perfusion-weighted data is typically relevant for a classification of the lesion. In particular the PI-RADS classification can be determined by means of the T2-weighted data and the diffusion-weighted data and the perfusion-weighted data. A PI-RADS value can be determined by means of the T2-weighted data and the diffusion-weighted data, and said value can be defined more precisely by means of the perfusion-weighted data. In the case of the presence of a lesion within the peripheral zone of the prostate it is therefore possible for example to differentiate between a PI-RADS value of 3 and 4 by means of the perfusion-weighted data from the lesion.

The PI-RADS classification allows a tumor of the prostate to be characterized particularly precisely and can also mean that a biopsy is not necessary. Based on the perfusion-weighted data the lesion can be characterized as malignant or benign.

This embodiment allows a frugal and individual application of a perfusion-weighted control sequence which comprises administering a contrast agent to the examination object.

An embodiment of the method provides that the examination region is a liver, upon actuation of the magnetic resonance device according to the at least one first control sequence an actuation of the magnetic resonance device takes places according to a T1-weighted control sequence and a T2-weighted control sequence without administering contrast agent to the examination object, and the first data comprises T1-weighted data and T2-weighted data.

The T1-weighted data and the T2-weighted data are typically image data. In the case of a liver, T2-weighted data and/or diffusion-weighted data, which are generated by means of the at least one first control sequence, can typically indicate a presence of a cyst and/or a hemangioma. In particular, the analysis of the first data comprising T1-weighted data and T2-weighted data of the examination region, i.e. the liver, a combined evaluation of the T1-weighted data and T2-weighted data as regards a property, in particular as regards a presence of a cyst and/or a hemangioma, can take place. The first data according to this embodiment is typically sufficient to detect or rule out a presence of a cyst and/or a hemangioma.

If the result comprises, for example, a presence of a cyst and/or a hemangioma in the examination region, at the selection stage a termination of the actuation of the magnetic resonance device preferably takes place. Further data acquired by means of a further control sequence, in particular a further control sequence using contrast agent, such as for example a T1-weighted control sequence and/or a T2-weighted control sequence and/or a diffusion-weighted control sequence and/or a perfusion-weighted control sequence each with contrast agent, would not deliver any further relevant information as regards the cyst and/or the hemangioma in this case. The shortened examination by means of the T1-weighted control sequence and the T2-weighted control sequence without contrast agent in the context of the at least one first control sequence is sufficient for a detection and/or diagnosis of a cyst and/or a hemangioma.

This embodiment thus enables an informative basis as regards a disease of the liver, in particular at an early stage after an actuation of the magnetic resonance device according to a T1-weighted control sequence and a T2-weighted control sequence without administering a contrast agent. This informative basis can in particular enable an efficient further process of the examination by means of a dedicated selection of an option. In particular, administering a contrast agent to the examination object only takes place if this is required for a diagnosis.

In the case of a liver, T1-weighted data which is generated by means of the at least one first control sequence can typically indicate a presence of hemochromatosis, i.e. diffuse liver disease. The option of selecting a Dixon VIBE control sequence can then be selected as the further control sequence and the further data can comprise image data having a DIXON contrast. The first control sequence can also comprise a Dixon VIBE control sequence and the first data can comprise image data having a DIXON contrast. A fat content of the liver can indicate a diffuse fat deposition in the liver by means of image data having a DIXON contrast. According to an embodiment further control sequences can be performed to quantify a fat content and/or iron content in the liver.

An embodiment of the method provides that, when choosing, a selection of at least one of the following control sequences as the further control sequence takes place:
Spectroscopy control sequence
Elastography control sequence
Diffusion-weighted control sequence
T1-weighted control sequence with administering of contrast agent to the examination object.

A spectroscopy control sequence allows an analysis of chemical substances in the examination region. An elastography control sequence allows a determination of an elasticity of an organ. A diffusion-weighted control sequence allows the representation of a diffusion movement of water molecules within the examination region. A T2-weighted control sequence allows a representation of the examination region, in which the T2 relaxation time of the tissue to be represented primarily determines the contrast. In the case of image data generated by means of a T2-weighted control sequence stationary fluids typically appear hyperintense.

A T1-weighted control sequence allows a representation of the examination region, in which the T1 relaxation time of the tissue to be represented primarily determines the contrast. In the case of image data generated by means of a T1-weighted control sequence fat typically appears hyperintense. If in addition a contrast agent is administered, typically intravenously, to the examination object, the contrast changes depending on the contrast agent used and the weighting of the control sequence.

The possible further control sequences mentioned in this embodiment allow a needs-driven, extensive diagnosis of the examination object and/or a gradual and justified procedure for the actuation of the magnetic resonance device depending on the examination region.

If the examination region comprises the liver and if the first data comprises T1-weighted data and T2-weighted data without the administering of contrast agent to the examination object, when selecting at least one of the named control sequences as the further control sequence the liver can be characterized particularly well. This enables the identification of a plurality of diseases. By taking the result into consideration when selecting the further control sequence, an indication of a disease can be validated by the further control sequence based on the T1-weighted data and T2-weighted data. In particular further data generated by means of a spectroscopy control sequence can indicate a fat content and/or iron content in the examination region. Further data generated by means of an elastography control sequence can indicate a stiffness of the liver, in particular a fibrosis.

An embodiment of the method provides that the examination region is a female breast. Upon actuation of the magnetic resonance device according to the at least one first control sequence, an actuation of the magnetic resonance device takes place according to a perfusion-weighted control sequence. The first data can include perfusion-weighted data, the result can include a presence of a lesion, and, when choosing, a selection of a T2-weighted control sequence takes place.

The perfusion-weighted data is typically image data. In the case of a breast, perfusion-weighted data which is generated by means of the at least one first control sequence can typically indicate a presence of a lesion. In particular, the analysis of the first data comprising perfusion-weighted data of the examination region, i.e. the breast as regards a property, in particular as regards a presence of a lesion, can take place. The first data according to this embodiment is typically sufficient to detect or rule out a presence of a lesion.

If the result comprises, for example, that no lesion is present in the examination region, at the selection stage a termination of the actuation of the magnetic resonance device preferably takes place.

If the result comprises for example a presence of a lesion in the examination region, at the selection stage a selection of at least one of the following control sequences as the further control sequence preferably takes place:

T2-weighted control sequence without administering of contrast agent to the examination object
T2-weighted control sequence with administering of contrast agent to the examination object
Elastography control sequence
Diffusion-weighted control sequence.

In the case of the presence of a lesion in the breast, T2-weighted data is typically relevant for a classification of the lesion. This embodiment thus enables an early, meaningful diagnosis as regards a lesion in the breast. It is therefore possible for example to draw a conclusion on the presence of a lesion based on the first data, and the further control sequence can be selected accordingly in the case of a characterization being required. This allows a short examination duration and a reliable diagnosis.

An embodiment of the method provides that the examination region is a female breast, upon actuation of the magnetic resonance device according to the at least one first control sequence an actuation of the magnetic resonance device takes place according to a T1-weighted control sequence, the first data comprises T1-weighted data, the result comprises a presence of a lesion and, when choosing, a selection of a further T1-weighted control sequence takes place. The further T1-weighted control sequence preferably differentiates itself from the T1-weighted control sequence in a dynamic phase and/or a spatial resolution and/or a signal-to-noise ratio, wherein image data generated by the further T1-weighted control sequence has a higher quality than the first data.

Furthermore, the disclosure is based on a magnetic resonance device with a controller comprising an actuation unit. The actuation unit is embodied to carry out a method according to the disclosure for actuating a magnetic resonance device.

For this purpose, in an exemplary embodiment, the actuation unit includes an input, a processor, and an output. In an exemplary embodiment, the actuation unit includes processor circuitry that is configured to perform one or more operations/functions of the actuation unit.

At least a first control sequence and/or a trained function and/or a neural network and/or a further control sequence can be made available to the actuation unit via the input. Further functions, algorithms or parameters required in the method can be provided to the actuation unit via the input. The property and/or the result and/or the further control sequence and/or an information about a termination of the actuation of the magnetic resonance device and/or further results of an embodiment of the method according to the disclosure can be made available via the output. The actuation unit can be integrated into the magnetic resonance device. The actuation unit can also be installed separately from the magnetic resonance device. The actuation unit can be connected (wirelessly or wired) to the magnetic resonance device.

Embodiments of the magnetic resonance device according to the disclosure are configured similarly to the embodiments of the method according to the disclosure. The magnetic resonance device can have further control components which are necessary and/or advantageous for carrying out a method according to the disclosure. The magnetic resonance device can also be configured to transmit control signals and/or to receive and/or process control signals in order to carry out a method according to the disclosure. The actuation unit is preferably part of the controller of the magnetic resonance device according to the disclosure. In a memory store unit of the actuation unit, computer programs and other software can be stored, by means of which the processor unit of the actuation unit automatically controls and/or carries out a sequence of a method according to the disclosure.

A computer program product according to the disclosure is directly loadable into a memory store unit of a programmable actuation unit and has program code means in order to carry out an inventive method when the computer program product is executed in the actuation unit. This means the inventive method can be performed quickly and robustly, and can be identically repeated. The computer program product is configured such that it can carry out the inventive method steps by means of the actuation unit. Therefore, the actuation unit must have the necessary specifications such as, for example, a suitable RAM, a suitable graphics card or a suitable logic unit, in order to be able to perform the respective method steps efficiently. The computer program product is stored, for example, on an electronically readable medium or is deposited on a network or server from where it can be loaded into the processor of a local actuation unit which can be directly connected to the magnetic resonance device or embodied as part of the magnetic resonance device. Furthermore, control information of the computer program product can be stored on an electronically readable data carrier. The control information of the electronically readable data carrier can be designed such that when the data carrier is used in an actuation unit of a magnetic resonance device it can perform an inventive method. Examples of electronically readable data carriers are a DVD, a magnetic tape or a USB stick, on which electronically readable control information, in particular software, is stored. If this control information (software) is read from the data carrier and stored in a controller and/or actuation unit of a magnetic resonance device, all inventive embodiments of the methods described above can be performed.

The disclosure also relates to an electronically readable data carrier on which a program is stored which is provided for carrying out a method for actuating a magnetic resonance device.

The advantages of the magnetic resonance device according to the disclosure, the computer program product according to the disclosure and the electronically readable data carrier according to the disclosure substantially correspond to the advantages of the method according to the disclosure for actuating a magnetic resonance device, as described in detail above. Features, advantages or alternative embodiments mentioned herein can likewise also be transferred to the other claimed subject matter and vice versa.

Figure 1:
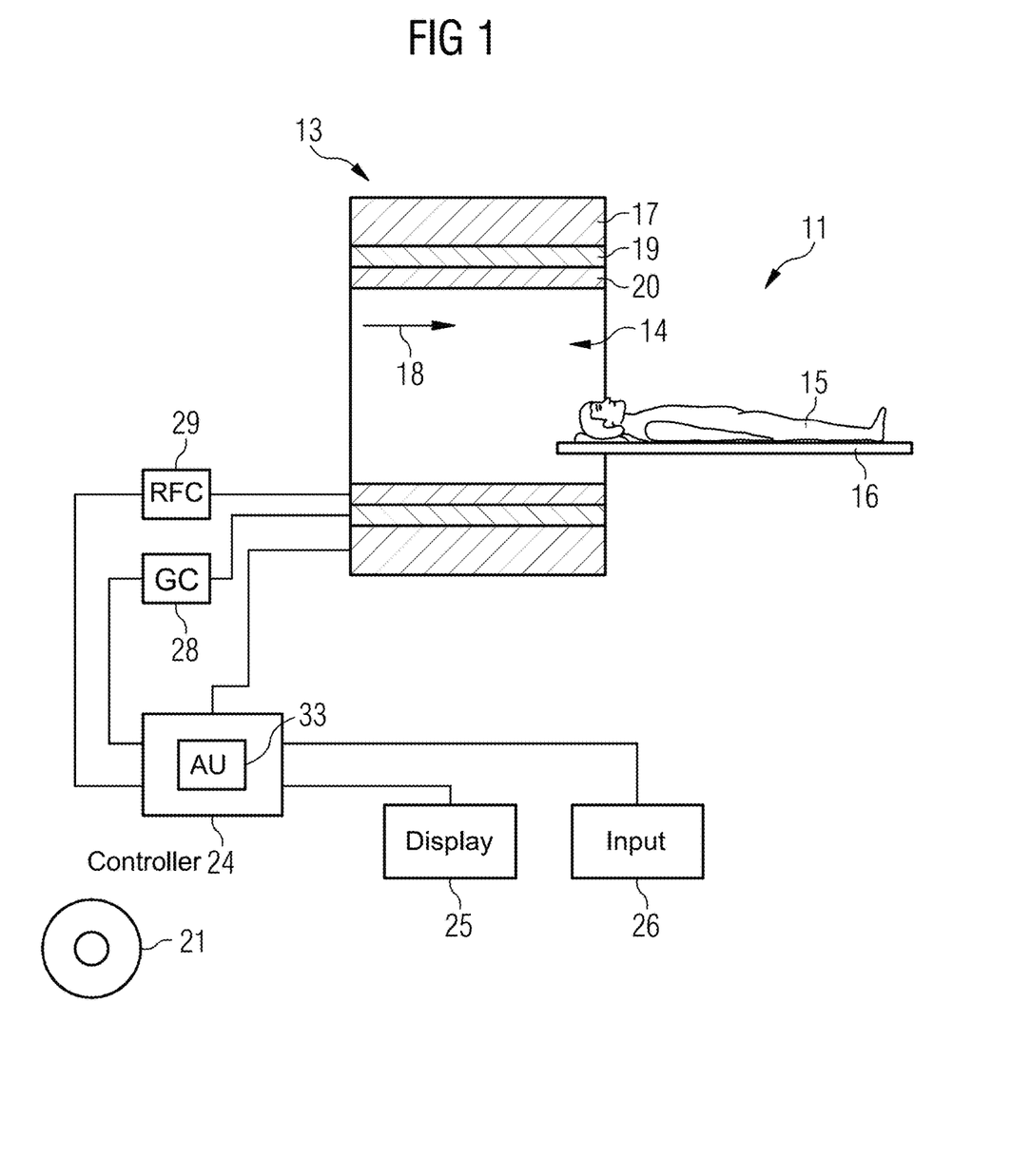
FIG. 1 shows a magnetic resonance device according to an exemplary embodiment.

FIG. 1 shows a magnetic resonance device 11, according to an exemplary embodiment, for carrying out a method according to the disclosure in a schematic representation. In an exemplary embodiment, the magnetic resonance device 11 comprises a detector unit formed of a magnet unit 13 with a main magnet 17 for generating a strong and, particularly, constant main magnetic field 18. Furthermore, the magnetic resonance device 11 has a cylindrical patient receiving region 14 for accommodating a patient 15, wherein the patient receiving region 14 is cylindrically enclosed in a peripheral direction by the magnet unit 13. The patient 15 can be pushed by means of a patient support apparatus 16 of the magnetic resonance device 11 into the patient receiving region 14. For this purpose, the patient support apparatus 16 has a patient couch which is arranged movably within the magnetic resonance device 11.

The magnet unit 13 also has a gradient coil unit 19 which is used for position encoding during an imaging process. The gradient coil unit 19 is actuated by means of a gradient controller 28. Furthermore, the magnet unit 13 has a radio-frequency antenna unit 20 which, in the case shown, is configured as a body coil permanently integrated into the magnetic resonance device 11, and a radio-frequency antenna controller 29 for an excitation of a polarization which occurs in the main magnetic field 18 generated by the main magnet 17. The radio-frequency antenna unit 20 is actuated by the radio-frequency antenna controller 29 and radiates high-frequency radio-frequency pulses into an examination space which is substantially formed by the patient receiving region 14.

In an exemplary embodiment, the magnetic resonance (MR) device 11 includes a controller 24 configured to control the main magnet 17, the gradient controller 28, and the radio-frequency antenna controller 29. The controller 24 centrally controls the magnetic resonance device 11, for example, the execution of control sequences. Furthermore, the controller 24 comprises a reconstruction unit (not shown in detail) for reconstructing medical image data which is acquired during the magnetic resonance examination. In an exemplary embodiment, the controller 24 includes processor circuitry that is configured to perform one or more functions/operations of the MR device 11.

The magnetic resonance device 11 can include a display unit 25. Control information such as, for example, control parameters and reconstructed image data can be displayed for a user on the display unit 25, for example on at least one monitor. In addition, the magnetic resonance device 11 has an input unit 26 by means of which information and/or control parameters can be input by a user during a scanning procedure. The controller 24 can comprise the gradient controller 28 and/or the radio-frequency antenna controller 29 and/or the display unit 25 and/or the input unit 26.

In an exemplary embodiment, the controller 24 further comprises an actuation unit 33. In an exemplary embodiment, the actuation unit 33 is also configured to perform a method for actuating a magnetic resonance device 11. In an exemplary embodiment, the actuation unit 33 has computer programs and/or software which can be directly loaded into a storage unit of the actuation unit 33 not shown in further detail, having program means in order to execute a method for actuating a magnetic resonance device 11 when the computer programs and/or software are executed in the actuation unit 33. For this purpose, in an exemplary embodiment, the actuation unit 33 has a processor (not disclosed in further detail) which is configured to execute the computer programs and/or software. Alternatively, the computer programs and/or software can also be stored on an electronically readable data carrier 21 configured separately from the controller 24 and/or the actuation unit 33, wherein a data access by the actuation unit 33 can take place on the electronically readable data carrier 21 via a data network. In an exemplary embodiment, the actuation unit 33 includes processor circuitry that is configured to perform one or more functions/operations of the actuation unit 33.

The display unit 25 is in particular embodied to display a preselection which was automatically determined by the actuation unit 33 based on the result. The input unit 26 is embodied in such a way that a user can confirm and/or reject a preselection.

The magnetic resonance device 11 shown can naturally comprise further components which magnetic resonance devices 11 typically have. A general mode of operation of a magnetic resonance device 11 is also known to the person skilled in the art so a detailed description of the further components is not included. The magnetic resonance device 11 is thus designed, together with the actuation unit 33, to perform an inventive method.

A method for actuating a magnetic resonance device 11 can also exist in the form of a computer program product which implements the method on the actuation unit 33 when it is executed on the actuation unit 33. An electronically readable data carrier 21 with electronically readable control information stored thereon can also be provided, said control information comprising at least one computer program product such as just described and being configured such that, on use of the data carrier 21 in an actuation unit 33 of a magnetic resonance device 11, said control information performs the method described.

Figure 2:
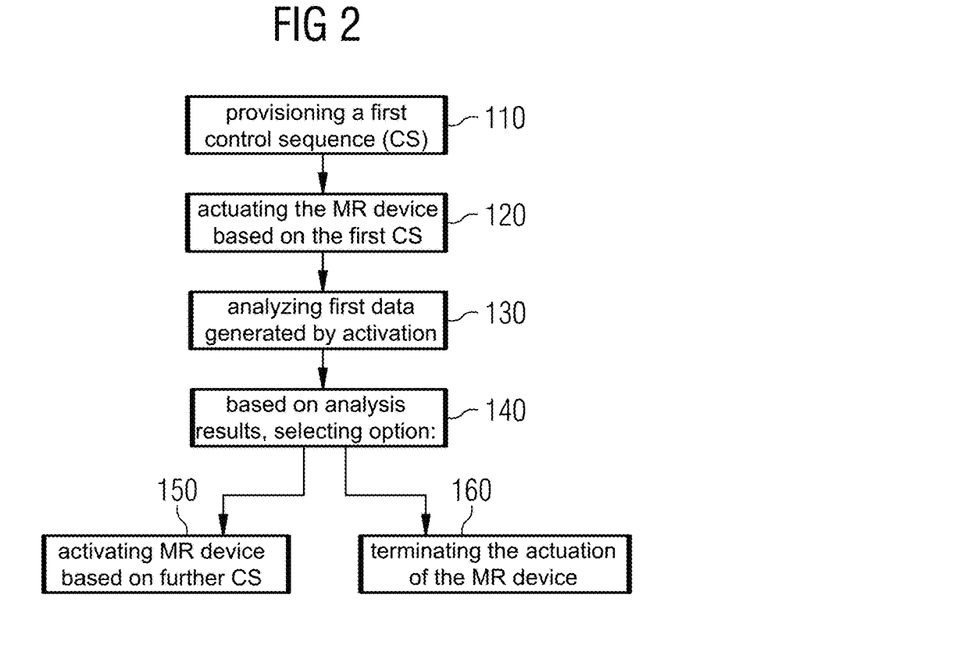
FIG. 2 shows a flowchart of a method according to an exemplary embodiment.

FIG. 2 shows a flow diagram of a first embodiment of a method according to an exemplary embodiment of the disclosure. The method according to the disclosure for an actuation of a magnetic resonance device 11 for capturing image data from an examination region of an examination object 15 starts with method step 110, the provision of at least one first control sequence. Method step 120 provides for the actuation of the magnetic resonance device 11 according to the at least one first control sequence, wherein first data is captured from the examination object. In the following method step 130, an analysis of the first data as regards a property takes place, wherein a result is generated. Based on the result a selection of one of the two following options takes place in method step 140: Selection of a further control sequence according to which further control sequence the magnetic resonance device 11 is actuated, or a termination of the actuation of the magnetic resonance device 11. The selected option is then executed, i.e. an actuation of the magnetic resonance device 11 according to the further control sequence in method step 150, or a termination of the actuation of the magnetic resonance device 11 in method step 160.

Figure 3:
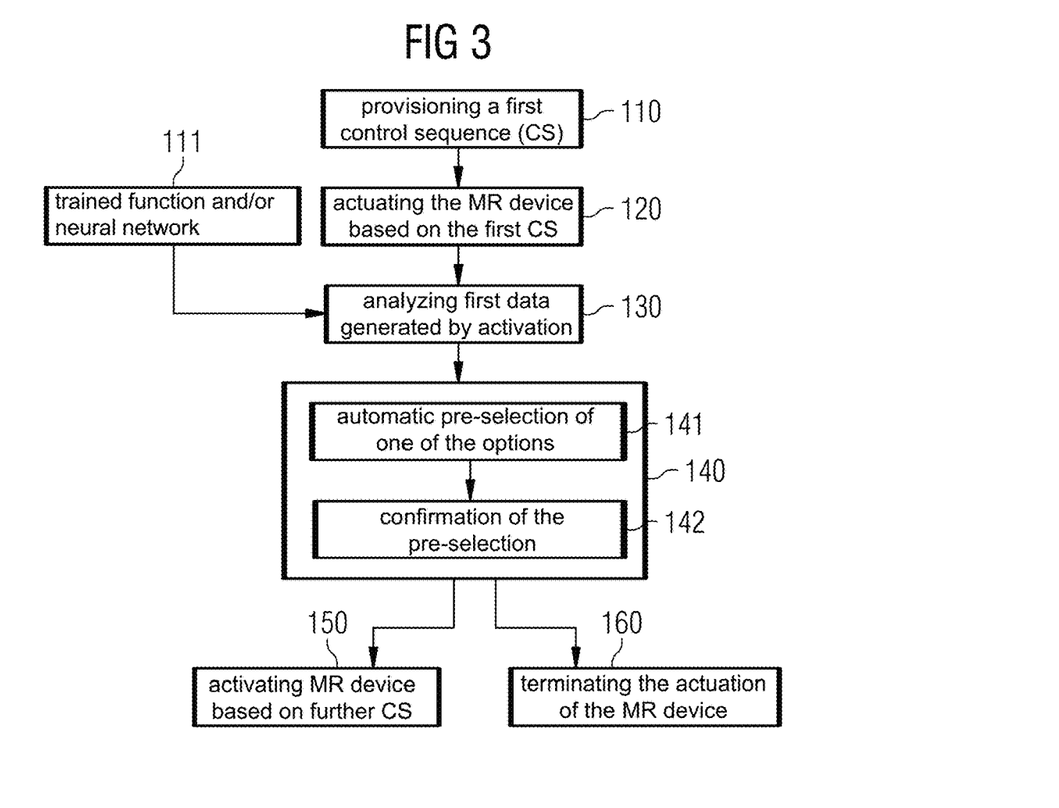
FIG. 3 shows a flowchart of a method according to another exemplary embodiment.

FIG. 3 shows a flow diagram of a second embodiment of a method according to an exemplary embodiment of the disclosure. This embodiment differs from the embodiment shown in FIG. 2 in the method steps 111, 141 and 142. In an exemplary embodiment, the method steps 111 and 140 are optional and independent of one another so that one or more both can be omitted or used in the variant shown in FIG. 2.

Method step 111 provides for a provision of a trained function and/or a neural network. The trained function and/or the neural network is used in the analysis of the first data in method step 130. As an option method step 140 can comprise an automatic preselection of one of the two options in method step 141 and a confirmation of the preselection by a user in method step 142.

Although the disclosure has been illustrated and described in detail by the preferred exemplary embodiments, the disclosure is not restricted by the examples disclosed and other variations can be derived therefrom by a person skilled in the art without departing from the protective scope of the disclosure.

Any connection or coupling between functional blocks, devices, components of physical or functional units shown in the drawings and described hereinafter may be implemented by an indirect connection or coupling. A coupling between components may be established over a wired or wireless connection. Functional blocks may be implemented in hardware, software, firmware, or a combination thereof.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

For the purposes of this discussion, the term "processor circuitry" shall be understood to be circuit(s), processor(s), logic, or a combination thereof. A circuit includes an analog circuit, a digital circuit, state machine logic, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

EXAMPLES

1. A method for an actuation of a magnetic resonance device for capturing image data from an examination region of an examination object comprising the following method steps:
   Provision of at least one first control sequence
   Actuation of the magnetic resonance device according to the at least one first control sequence, wherein first data is captured from the examination object,
   Analysis of the first data as regards a property,
   wherein a result is generated, and
   Selection of one of the two following options, based on the result:
      Selection of a further control sequence, or
      Termination of the actuation of the magnetic resonance device 2. An embodiment of the method as described in embodiment 1, wherein the method comprises a provision of a trained neural network and the analysis of the first data takes place using the trained neural network.

3. The embodiment of the method as described in one of the preceding examples, wherein upon selection of a further control sequence in a following method step an actuation of the magnetic resonance device according to the further control sequence takes place.

4. The example of the method as described in one of the preceding examples, wherein the selection comprises an automatic preselection of one of the two options and a confirmation of the preselection by a user.

5. The example of the method as described in one of the preceding examples, wherein the property comprises at least one of the following features: an artifact; a susceptibility artifact; a lesion; a cyst; a hemangioma; a size of a structure; a texture of a structure; a movement of the examination object during the actuation of the magnetic resonance device according to the at least one first control sequence; a quality of the first data; and/or an abnormality.

6. The example of the method as described in one of the preceding examples, wherein the result comprises a presence of the property and/or a comparison of a value characterizing the property with a reference value.

7. The example of the method as described in one of the preceding examples, wherein the result comprises a presence of a susceptibility artifact and, when choosing, a selection of a further control sequence for reducing metal artifacts takes place.

8. The example of the method as described in one of the preceding examples, wherein the result comprises a presence of a movement above a threshold value and, when choosing, a selection of a movement-insensitive control sequence takes place.

9. The example of the method as described in one of the preceding examples, wherein the examination region is a prostate.

10. The example of the method as described in one of the preceding examples, in particular as described in example 9, wherein upon actuation of the magnetic resonance device according to the at least one first control sequence an actuation of the magnetic resonance device takes place according to a T2-weighted control sequence and a diffusion-weighted control sequence, and the first data comprises T2-weighted data and diffusion-weighted data.

11. The example of the method as described in one of the preceding examples, in particular as described in example 9 or 10, wherein the result comprises a presence of a lesion and, when choosing, a selection of a perfusion-weighted control sequence as the further control sequence takes place.

12. The example of the method as described in one of the preceding examples, in particular as described in example 9 or 10, wherein the result comprises a presence of a lesion and, when choosing, a termination of the actuation of the magnetic resonance device takes place.

13. The example of the method as described in one of the examples 1 to 8, wherein the examination region is a liver.

14. The example of the method as described in one of the preceding examples, in particular as described in example 13, wherein upon actuation of the magnetic resonance device according to the at least one first control sequence an actuation of the magnetic resonance device takes place according to a T1-weighted control sequence and a T2-weighted control sequence without administering contrast agent to the examination object, and the first data comprises T1-weighted data and T2-weighted data.

15. The example of the method as described in one of the preceding examples, in particular as described in example 14, wherein the result comprises a presence of a cyst and/or a hemangioma and, when choosing, a termination of the actuation of the magnetic resonance device takes place.

16. An example of the method as described in example 14, wherein, when choosing, a selection of at least one of the following control sequences as the further control sequence takes place:
Spectroscopy control sequence;
Elastography control sequence;
Diffusion-weighted control sequence; and/or
T1-weighted control sequence with administering of contrast agent to the examination object.

17. The example of the method as described in one of the examples 1 to 8, wherein the examination region is a female breast.

18. The example of the method as described in one of the preceding examples, in particular as described in example 17, wherein upon actuation of the magnetic resonance device according to the at least one first control sequence an actuation of the magnetic resonance device takes place according to a perfusion-weighted control sequence, and the first data comprises perfusion-weighted data.

19. The example of the method as described in one of the preceding examples, in particular as described in example 17 or 18, wherein the result comprises a presence of a lesion and, when choosing, a selection of a T2-weighted control sequence takes place.

The invention claimed is:

1. A method for an actuation of a magnetic resonance device for capturing image data from an examination region of an examination object, the method comprising:
provisioning at least one first control sequence that specifies an actuation of the magnetic resonance device for generating image data;
actuating the magnetic resonance device, according to the at least one first control sequence, to capture first image data from the examination object during an examination, the first image data being generated by the actuation of the magnetic resonance device;
analyzing the first image data with respect to a property to generate a result indicative of an illness, the analysis of the first image data including a comparison of a value characterizing the property with a threshold value, wherein the result indicative of the illness is generated based on the comparison;
during the same examination and in response to the value being greater than the threshold value, automatically selecting a further control sequence configured to generate a contrast adapted for diagnosis of the illness and that specifies a subsequent actuation of the magnetic resonance device to capture second image data from the examination object during the same examination, the automatic selection of the further control sequence being based on the illness indicated by the result; and
during the same examination and in response to the value being less than the threshold value, automatically terminating the actuation of the magnetic resonance device.

2. The method as claimed in claim 1, further comprising:
provisioning a trained function and/or a neural network, wherein the analysis of the first image data is performed using the trained function and/or the neural network.

3. The method as claimed in claim 1, wherein the selection of the further control sequence comprises:
an automatic preselection of the selection of the further control sequence in response to the value being greater than the threshold value, and the termination of the actuation of the magnetic resonance device in response to the value being less than the threshold value; and
a confirmation of the preselection by a user.

4. The method as claimed in claim 1, wherein the property comprises: an artifact; a susceptibility artifact; a lesion; a cyst; a hemangioma; a size of a structure; a texture of a structure; a movement of the examination object during the actuation of the magnetic resonance device according to the at least one first control sequence; and/or an abnormality.

5. The method as claimed in claim 1, wherein the result comprises a presence of the property.

6. The method as claimed in claim 1, wherein the result comprises a presence of a susceptibility artifact, the selected further control sequence including a control sequence configured to reduce metal artifacts.

7. The method as claimed in claim 1, wherein the result comprises a presence of a movement above a movement threshold value, the selected further control sequence including a movement-insensitive control sequence.

8. The method as claimed in claim 1, wherein:
the examination region is a prostate;
upon actuation of the magnetic resonance device according to the at least one first control sequence, an actuation of the magnetic resonance device is performed according to a T2-weighted control sequence and a diffusion-weighted control sequence; and
the first image data comprises T2-weighted data and diffusion-weighted data.

9. The method as claimed in claim 1, wherein the result comprises a presence of a lesion, the selected further control sequence including a perfusion-weighted control sequence.

10. The method as claimed in claim 1, wherein:
the examination region is a liver;
upon actuation of the magnetic resonance device according to the at least one first control sequence, an actuation of the magnetic resonance device takes places according to a T1-weighted control sequence and a T2-weighted control sequence without administering contrast agent to the examination object; and
the first image data comprises T1-weighted data and T2-weighted data.

11. The method as claimed in claim 1, wherein, the selected further control sequence includes:
spectroscopy control sequence;
elastography control sequence;
diffusion-weighted control sequence; and/or
T1-weighted control sequence with administering of contrast agent to the examination object.

12. The method as claimed in claim 1, wherein:
the examination region is a female breast;
upon actuation of the magnetic resonance device according to the at least one first control sequence, an actuation of the magnetic resonance device takes place according to a perfusion-weighted control sequence;
the first image data comprises perfusion-weighted data;
the result comprises a presence of a lesion; and
the selected further control sequence includes a T2-weighted control sequence.

13. A non-transitory computer-readable storage medium with an executable program stored thereon, that when executed, instructs a processor to perform a method comprising:
provisioning at least one first control sequence that specifies an actuation of the magnetic resonance device for generating image data;
actuating the magnetic resonance device, according to the at least one first control sequence, to capture first image data from the examination object during an examination, the first image data being generated by the actuation of the magnetic resonance device;
analyzing the first image data with respect to a property to generate a result indicative of an illness, the analysis of the first image data including a comparison of a value characterizing the property with a threshold value, wherein the result indicative of the illness is generated based on the comparison;
during the same examination and in response to the value being greater than the threshold value, automatically selecting a further control sequence configured to generate a contrast adapted for diagnosis of the illness and that specifies a subsequent actuation of the magnetic resonance device to capture second image data from the examination object during the same examination, the automatic selection of the further control sequence being based on the illness indicated by the result; and
during the same examination and in response to the value being less than the threshold value, automatically terminating the actuation of the magnetic resonance device.

14. A magnetic resonance (MR) device comprising:
a MR scanner; and
a controller configured to:
provision at least one first control sequence that specifies an actuation of the MR scanner for generating image data;
actuate the MR scanner, according to the at least one first control sequence, to capture first image data from the examination object during an examination, the first image data being generated by the actuation of the MR scanner;
analyze the first image data with respect to a property to generate a result indicative of an illness, the analysis of the first image data including a comparison of a value characterizing the property with a threshold value, wherein the result indicative of the illness is generated based on the comparison;
during the same examination and in response to the value being greater than the threshold value, automatically selecting a further control sequence configured to generate a contrast adapted for diagnosis of the illness and that specifies a subsequent actuation of the MR scanner to capture second image data from the examination object during the same examination, the selection of the further control sequence being based on the illness indicated by the result; and
during the same examination and in response to the value being less than the threshold value, automatically terminate the actuation of the MR scanner.

15. The MR device as claimed in claim 14, wherein the controller comprises an actuation unit that is configured to perform the provisioning, actuating, analyzing, automatic selection, and automatic termination.

16. The method as claimed in claim 1, wherein the first data comprises a spatially resolved signal intensity in k-space and/or in an image space.

17. A method for an actuation of a magnetic resonance device for capturing image data from an examination region of an examination object, the method comprising:
provisioning at least one first control sequence that specifies an actuation of the magnetic resonance device for generating image data with a contrast;
actuating the magnetic resonance device, according to the at least one first control sequence, to capture first image data from the examination object during an examination;

analyzing the first image data with respect to a property to generate a result, the analysis of the first image data including a comparison of a value characterizing the property with a threshold value, wherein the result is generated based on the comparison, and wherein the property includes: an artifact, a susceptibility artifact, a lesion, a cyst, a hemangioma, a size of a structure, a texture of a structure, a movement of the examination object during the actuation of the magnetic resonance device according to the at least one first control sequence, and/or an abnormality; and during the same examination and based on the comparison, automatically selecting a further control sequence that specifies a subsequent actuation of the magnetic resonance device to capture second image data from the examination object during the same examination.

18. The method as claimed in claim 17, wherein, the selected further control sequence includes: spectroscopy control sequence; elastography control sequence;

diffusion-weighted control sequence; and/or T1-weighted control sequence with administering of contrast agent to the examination object.

19. The method as claimed in claim 1, further comprising, in response to the selection of the further control sequence, automatically actuating the magnetic resonance device according to the further control sequence to automatically capture the second image data from the examination object during the same examination.

\* \* \* \* \*